United States Patent [19]

Lan et al.

[11] Patent Number: 4,828,819

[45] Date of Patent: May 9, 1989

[54] COMPOSITIONS CONTAINING BIS-(QUATERNARY AMMONIUM) DERIVATIVES FOR THE TREATMENT OF KERATIN MATERIALS AND NATURAL NON-KERATIN OR SYNTHETIC TEXTILE MATERIALS

[75] Inventors: Gérard Lan, Saint Gratien; Serge Forestier, Claye Souilly, both of France

[73] Assignee: L'Oreal, Paris, France

[21] Appl. No.: 207,624

[22] Filed: Jun. 16, 1988

Related U.S. Application Data

[60] Division of Ser. No. 751,454, Jul. 2, 1985, Pat. No. 4,774,075, which is a continuation of Ser. No. 270,798, Jun. 5, 1981, abandoned.

[30] Foreign Application Priority Data

Jun. 6, 1980 [FR] France ............................. 80 12687
Aug. 28, 1980 [FR] France ............................. 80 18711

[51] Int. Cl.⁴ .................... A61K 7/06; A61K 7/08; A61K 7/135; A61K 9/12
[52] U.S. Cl. ........................................... 424/47; 8/406; 132/202; 424/62; 424/70; 424/71; 424/72; 514/937; 514/938; 514/944
[58] Field of Search ............... 424/47, 70; 260/404.5; 132/7

[56] References Cited

U.S. PATENT DOCUMENTS

| 2,850,529 | 9/1958 | Pinson, Jr. ........................... | 424/70 |
| 3,678,157 | 7/1972 | Kalopissis et al. .................... | 424/70 |
| 3,882,114 | 5/1975 | Kalopissis et al. .................... | 424/70 |

FOREIGN PATENT DOCUMENTS

| 1149363 | 5/1963 | Fed. Rep. of Germany ........ | 424/70 |
| 1110724 | 10/1959 | France ................................. | 424/70 |
| 1190096 | 10/1959 | France ................................. | 424/70 |
| 1347612 | 11/1963 | France ................................. | 424/70 |
| 701209 | 12/1953 | United Kingdom ................ | 424/70 |
| 706421 | 3/1954 | United Kingdom ................ | 424/70 |
| 756706 | 9/1956 | United Kingdom ................ | 424/70 |
| 969285 | 9/1964 | United Kingdom ................ | 424/70 |
| 1067519 | 5/1967 | United Kingdom ................ | 424/70 |
| 1234408 | 6/1971 | United Kingdom ................ | 424/70 |
| 1237266 | 6/1971 | United Kingdom ................ | 424/70 |
| 1249477 | 10/1971 | United Kingdom ................ | 424/70 |
| 1253235 | 11/1971 | United Kingdom ................ | 424/70 |
| 1427601 | 3/1976 | United Kingdom ................ | 424/70 |
| 1467194 | 3/1977 | United Kingdom ................ | 424/70 |
| 1513672 | 6/1978 | United Kingdom ................ | 424/70 |
| 1546162 | 5/1979 | United Kingdom ................ | 424/70 |
| 1568989 | 6/1980 | United Kingdom ................ | 424/70 |
| 1570220 | 6/1980 | United Kingdom ................ | 424/70 |

Primary Examiner—Dale R. Ore
Attorney, Agent, or Firm—Fleit, Jacobson, Cohn & Price

[57] ABSTRACT

The composition of the invention comprises, in a medium suitable for the treatment of keratin materials, and natural non-keratin or synthetic textile materials, at least one bis-(quaternary ammonium) derivative having the formula:

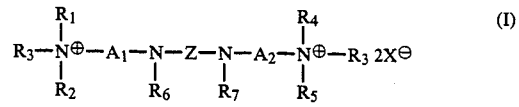

in which $R_1$, $R_2$, $R_4$ and $R_5$ are identical or different and denote lower alkyl or lower hydroxyalkyl radicals, $R_3$ is an alkyl, cycloalkyl, alkenyl, hydroxyalkyl or optionally substituted aralkyl radical containing a maximum of 20 carbon atoms, $A_1$ and $A_2$, which are identical or different, represent optionally substituted alkylene or arylene radicals which can contain up to 20 carbon atoms, $Z=-SO_2-$ or $-(CO)_p$, in which $p=1$ or 2, $R_6$ and $R_7$, which are identical or different, are hydrogen atoms or lower alkyl radicals, or alternatively, if $Z=-(CO)_p$ in which $p=1$, $R_6$ and $R_7$ can together form a group:

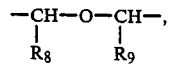

$R_8$ and $R_9$ being hydrogen atoms or lower alkyl radicals, and $X^\ominus$ denotes an inorganic or organic anion derived from low molecular weight acids.

20 Claims, No Drawings

COMPOSITIONS CONTAINING BIS-(QUATERNARY AMMONIUM) DERIVATIVES FOR THE TREATMENT OF KERATIN MATERIALS AND NATURAL NON-KERATIN OR SYNTHETIC TEXTILE MATERIALS

This is a divisional of application Ser. No. 751,454 filed July 2, 1985, now U.S. Pat. No. 4,774,075, which is a continuation application of Ser. No. 270,798, filed June 5, 1981, now abandoned.

The present invention relates to compositions containing bis-(quaternary ammonium) derivatives, for the treatment of keratin materials, such as hair, skin, nails and wool, and of natural non-keratin or synthetic textile materials, and to compounds used in these compositions.

It is known to use cosmetic compositions based on quaternary ammonium derivatives for treating the hair.

These compositions, used in particular as post-shampoo rinsing products, are usually presented in the form of milky liquids, balms or creams and have the disadvantage of weighing down the hair treated, both because of the nature of the quaternary ammonium derivatives used and because of the nature of the adjuvants required to give these compositions the desired appearance, viscosity and softness effects. Because of their weighing-down effect, these compositions are preferably used in the treatment of dry or damaged hair.

We have now discovered, according to the present invention, that the use of a particular class of bis-(quaternary ammonium) derivative makes it possible to prepare compositions for use in the treatment of keratin materials and natural non-keratin or synthetic textile materials, which compositions generally constitute limpid, fluid or optionally thickened formulations, and that these compositions, when applied to any type of hair (dry hair, normal hair or hair which tends to become greasy), give the hair more lightness than the compositions containing the quaternary ammonium derivatives which have so far been used.

The compounds can be used in relatively small amounts for improving the comb-out, the softness, the shine, the hold and the bulk of the hair, and are furthermore well tolerated by the skin.

The present invention thus provides compositions suitable for use in the treatment of keratin materials and natural non-keratin or synthetic textile materials, which comprise, in a medium suitable for the treatment of these materials, at least one bis-(quaternary ammonium) derivative having the formula:

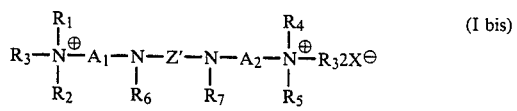

in which $R_1$, $R_2$, $R_4$ and $R_5$ are identical or different and denote lower alkyl or lower hydroxyalkyl radicals, $R_3$ is an alkyl, cycloalkyl, alkenyl, hydroxyalkyl or optionally substituted aralkyl radical containing a maximum of 20 carbon atoms, $A_1$ and $A_2$, which are identical or different, represent optionally substituted alkylene or arylene radicals which can contain up to 20 carbon atoms, $Z = -SO_2-$ or $-(CO)_p$, in which $p = 1$ or 2, $R_6$ and $R_7$, which are identical or different, are hydrogen atoms or lower alkyl radicals, or alternatively, if $Z = -(CO)_p$ in which $p = 1$, $R_6$ and $R_7$ can together form a group:

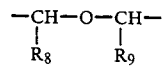

$R_8$ and $R_9$ being hydrogen atoms or lower alkyl radicals, and $X^{\ominus}$ denotes an inorganic or organic anion derived from low molecular weight acids, such as a halide anion, for example chloride or bromide, or a nitrate, sulphate, para-toluenesulphonate, methosulphate or ethosulphate anion.

In this specification, the term "lower alkyl radical" is to be understood as meaning a $C_1$ to $C_6$ alkyl radical.

In the compounds of the formula (I) used in the present invention, $R_1$, $R_2$, $R_4$ and $R_5$ preferably denote a lower alkyl radical, in particular methyl or ethyl; $R_3$ preferably denotes an alkyl radical, in particular a $C_8$ to $C_{18}$ alkyl radical; and $A_1$ and $A_2$ preferably denote an alkylene radical, in particular ethylene or trimethylene.

The present invention also provides a process for the treatment of keratin materials and natural nonkeratin or synthetic textile materials with the aid of the compositions defined above.

The present invention also provides the new compounds having the formula:

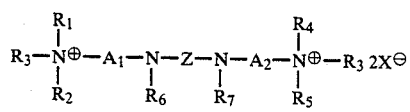

in which $R_1$, $R_2$, $R_4$ and $R_5$, $R_3$, $A_1$ and $A_2$ and $X^{\ominus}$ have the meanings indicated above for the formula (I), $Z' = -SO_2-$ or $-(CO)_p$, in which $p = 1$ or 2, and $R_6$ and $R_7$, which are identical or different, are hydrogen atoms or lower alkyl radicals, or alternatively, if $Z' = -(CO)_p$ in which $p = 1$, $R_6$ and $R_7$ can together form a group

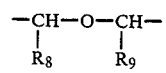

$R_8$ and $R_9$ being hydrogen atoms or lower alkyl radicals, with the proviso that, if $Z' = -(CO)_p$ in which $p = 1$, $R_3$ denotes an alkyl or hydroxyalkyl radical containing at least 4 carbon atoms, and if $Z' = -(CO)_p$ in which $p = 2$, $R_3$ does not denote an aralkyl radical.

The compounds according to the invention, most of which are water-soluble, can be obtained in accordance with a conventional process by the quaternisation of a tertiary diamine of the formula:

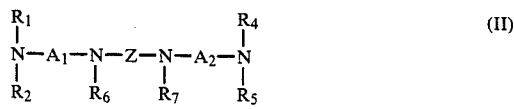

with a quaternising agent of the formula:

in which X preferably denotes a halogen atom.

The polycondensation reaction is carried out, for example, in a solvent which assists quaternisation reactions, or in a mixture of such solvents, such as water, dimethylformamide, acetone, methyl ethyl ketone, acetonitrile and lower alcohols, in particular methanol.

The reaction temperature is suitably from 10° to 150° C. and preferably from 20° to 100° C., and the reaction time depends on the nature of the solvent and the starting reactants.

It is possible to react the starting reactants in equimolecular amounts or to use an excess of quaternising agent.

As indicated above, the compounds corresponding to the formula (I) possess valuable properties when they are used in the treatment of keratin materials, such as hair, skin, nails and wool, and of natural non-keratin or synthetic textile materials.

The compositions for use in the treatment of the keratin materials and natural non-keratin or synthetic textile materials mentioned above are preferably aqueous compositions, which can be used as such, but which can also contain adjuvants normally used in compositions for the treatment of keratin materials or non-keratin textile materials.

The compositions according to the invention are applied to the materials indicated above in a sufficient amount and, after an interval of, say, 1 to 30 minutes, the materials are optionally rinsed.

The compounds of the formula (I) give particularly valuable results when they are applied in cosmetics and in particular when they are used for treating the hair.

The cosmetic compositions are suitably presented in the form of aqueous, alcoholic or aqueous-alcoholic solutions or in the form of creams, gels, emulsions or powders, or can be packaged in an aerosol in the presence of a propellant.

The adjuvants optionally present in these compositions are cosmetically acceptable adjuvants such as non-ionic, anionic, cationic or amphoteric surface-active agents which are well known in the state of the art, animal, mineral, vegetable or synthetic oils or waxes, fatty alcohols, anionic, cationic, non-ionic or amphoteric resins normally used in cosmetics, emulsifiers, sun filters, organic solvents, thickeners, opacifiers, preservatives, sequestering agents, anti-oxidants, perfumes, agents for imparting pearlescence, dyestuffs, pH modifiers, reducing agents, electrolytes, oxidising agents, natural substances, protein derivatives, anti-seborrhea or anti-dandruff agents, restructuring agents, and other substances active in the treatment, care or protection of the skin or hair.

These compositions can be used, in particular, as shampoos, as colouring or bleaching products, as rinsing lotions to be applied before or after shampooing, before or after colouring or bleaching or before or after perming or as styling or restructuring lotions, treating lotions, in particular anti-seborrhea or anti-dandruff lotions, brushing lotions, hair lacquers, wavesetting lotions, perming compositions, styling gels and hair-care creams.

The application of these compositions to the hair is optionally followed by rinsing, after an interval of, say, 1 to 30 minutes.

If the compounds used in the invention are applied in order to treat the hair, either in pre-treatment or post-treatment lotions or during the treatment, such as shampooing, dyeing, bleaching, wavesetting, or perming, they can substantially improve the properties of the hair by making the hair easier to comb out when wet or dry and by giving the hair hold, shine, softness, suppleness, manageability and antistatic properties when dry. The hair treated in this way is light, bouncy and bulky.

The bis-(quaternary ammonium) derivatives of the formula (I) should be used in the compositions according to the invention in sufficient amounts to obtain the desired result, and generally in amounts from 0.01 to 10% by weight and preferably from 0.1 to 5% by weight, relative to the total weight of the composition.

According to a first embodiment of the invention, the cosmetic compositions for the hair are treating compositions or pre-treatment or post-treatment compositions for the hair, such as rinsing lotions, wavesetting lotions, restructuring lotions, leave-on lotions or hair-care creams.

The pH of these compositions is generally from 2 to 11. The treating compositions or pre-treatment or post-treatment compositions can contain various adjuvants, in particular polyethylene glycols and their derivatives, anionic, cationic, amphoteric or non-ionic resins normally used in cosmetic compositions for the hair, pH modifiers, protein derivatives, such as quanternised or unquaternised protein hydrolysates, natural substances, such as plant extracts, fatty alcohols, such as optionally polyoxyethyleneated or polyglycerolated cetyl, stearyl, cetyl/stearyl or oleyl alcohol, animal, vegetable, mineral or synthetic oils or waxes, such as optionally oxyethyleneated vaseline oil (liquid petrolatum), corn oil, wheatgerm oil, olive oil, soya oil, castor oil or avocado oil, active substances, such as anti-seborrhea or anti-dandruff products, hair-restructuring agents, such as methylolated derivatives, and also other cosmetic adjuvants normally used in cosmetic compositions for the hair.

According to a preferred embodiment, the compositions for treating the hair, according to the invention, are shampoos which are essentially characterised in that they contain at least one anionic, non-ionic or amphoteric surface-active agent, or mixtures thereof, and a compound of the formula (I), in an aqueous medium. These compositions can also contain various adjuvants normally used in this type of composition, such as cationic surface-active agents, dyestuffs in the case of colouring shampoos, preservatives, thickeners, foam stabilisers, synergistic agents, softeners, sequestering agents, one or more cosmetic resins, perfumes, protein derivatives, natural substances, oils and also other adjuvants used in a shampoo. In these shampoos, the concentration of detergent is generally 2 to 50% by weight.

Amongst the non-ionic detergents, there may be mentioned, in particular, the condensation products of a monoalcohol, an alpha-diol, an alkylphenol, an amide or a diglycolamide with glycidol, such as the non-ionic surface-active agents described in French Pat. Nos. 2,091,516, 2,328,763 and 1,477,048, and also polyoxyethyleneated or polyglycerolated fatty alcohols, alkylphenols or acids with linear fatty chains having 8 to 30 carbon atoms and most frequently containing 2 to 30 mols of ethylene oxide, copolymers of ethylene oxide and propylene oxide, condensates of ethylene oxide and propylene oxide with fatty alcohols, polyoxyethyleneated fatty amides, polyoxyethyleneated fatty amines, ethanolamides, fatty acid esters of glycol, fatty acid esters of sorbitol and fatty acid esters of sucrose.

The anionic surface-active agents which can be used, optionally mixed with the non-ionic surface-active agents, are chosen, in particular, from amongst the alkali metal salts, the ammonium salts, the amine salts or the aminoalcohol salts of the following compounds:

alkyl-sulphates, alkyl-ether-sulphates, alkylamide-sulphates and alkylamido-ether-sulphates, alkylaryl-polyether-sulphates and monoglyceride-sulphates;

alkylsulphonates, alkylamindesulphonates, alkylarylsulphonates and α-olefinesulphonates;

alkyl-sulphosuccinates, alkyl-ether-sulphosuccinates and alkylamide-sulphosuccinates;

alkyl-sulphosuccinamates;

alkyl-sulphoacetates and alkyl-polyglycerolcarboxylates;

alkyl-phosphates and alkyl-ether-phosphates; and alkylsarcosinates, alkylpolypeptidates, alkylamidopolypeptidates, alkylisethionates and alkyltaurates, the alkyl radical in all these compounds being a linear chain having 12 to 30 carbon atoms; and fatty acids, such as oleic, ricinoleic, palmitic or stearic acid, acids derived from copra oil or from hydrogenated copra oil, and carboxylic acids of polyglycol ethers, corresponding to the formula:

$$Alk-(OCH_2-CH_2)_n-OCH_2-CO_2H$$

in which the substituent Alk corresponds to a linear chain having from 12 to 18 carbon atoms and in which n is an integer from 5 to 15. It is also possible to use other anionic detergents which are well known in the state of the art.

Amongst the amphoteric surface-active agents which can be used, there may be mentioned, more particularly, alkylamino monopropionates and dipropionates, betaines, such as N-alkylbetaines, N-alkylsulphobetaines and N-alkylamidobetaines, cycloimidinium compounds, such as alkylimidazolines, and asparagine derivatives. The alkyl group in these surface-active agents preferably has 1 to 22 carbon atoms.

The cosmetic compositions according to the invention can also be hair-dyeing compositions such as so-called oxidation dyeing compositions which contain oxidation dyestuff precursors, for example of the para- or ortho-type, and optionally couplers, in a basic medium preferably having a pH of 8 to 11, and which can also contain direct dyestuffs well known in the state of the art, or dyeing compositions for direct or semi-permanent coloration, which contain direct dyestuffs, such as nitro benzene derivatives, azo dyestuffs, anthraquinone dyestuffs, indamines, indoanilines or indophenols.

The compositions for treating the hair, according to the invention, can also be bleaching compositions which are in the form of, for example, powders, solutions, emulsions, gellable liquids or creams containing at least one bleaching agent, such as hydrogen peroxide, peroxides or solutions of per-salts (persulphates, perborates or percarbonates), and at least one compound of the formula (I).

Preferably, the bleaching compositions are in the form of creams or gellable liquids. These compositions are usually diluted at the time of use with a solution of hydrogen peroxide and/or per-salt and/or peroxide.

These compositions generally contain an alkalising agent such as ammonia.

These bleaching compositions can be applied in accordance with conventional techniques.

The compositions for treating the hair, according to the invention, can also be perming compositions.

The formulation of such perming compositions, comprising a reducing composition and an oxidising composition (neutraliser), is known and described in the works on cosmetology, in particular by E SIDI and C ZVIAK Problèmes Capillaires (Hair Problems), Paris 1966 (GAUTHIER-VILLARD).

According to the invention, at least one of the reducing or oxidising compositions contains a compound of the formula (I).

Apart from the reducing agent, the reducing compositions contain adjuvants which make it possible to present them in the form of, for example, lotions or a powder to be diluted in a liquid carrier.

The pH of these compositions for the first stage of perming is generally from 7 to 10.

The reducing compositions generally contain from 0.01 to 10% by weight of compound of the formula (I), and in particular from 0.1 to 5% by weight.

Apart from the oxidising agent, the oxidising or neutralising compositions applied in a second stage can contain conventional adjuvants.

The compounds of the formula (I) can of course be used in all the cosmetic formulations as additives for giving the hair characteristics of comb-out, softness, shine, lightness, hold and bulk, in addition to the properties which the compositions themselves are intended to give.

The compositions according to the invention can also be applied to the skin and can be presented in the various forms mentioned above. The bis-(quaternary ammonium) derivatives give the skin a softness to the touch.

In addition to the compounds of the formula (I), such compositions can contain various cosmetic adjuvants normally used for the skin, and in particular perfumes, dyestuffs, preservatives, sequestering agents, emulsifying agents, thickeners and sun filters.

The compositions constitute, especially, treating creams or lotions for the hands or face, antisunburn creams, tinted creams, make-up removal milks or lotions, shaving creams, foaming oils or liquids for the bath or shower, or deodorants which can be prepared in accordance with conventional processes.

The compositions according to the invention can also be used for finishing and rinsing wool and other natural or synthetic textile materials.

It should be noted that the compounds according to the invention also possess other valuable properties such as dispersing, emulsifying or flocculating properties.

The following Examples further illustrate the present invention.

Preparation Examples

EXAMPLE 1

46 g of 1,3-bis-(3-dimethylaminopropyl)-urea are dissolved in 100 g of acetone. 105 g of 1-bromodo-decane are added and the mixture is heated under reflux for 7 hours. The reaction mixture is left to cool and is then diluted with 400 cm³ of acetone. The solid is filtered off, washed with acetone and dried under reduced pressure. This yields 87 g of a white product melting at 108° C., which corresponds to the formula:

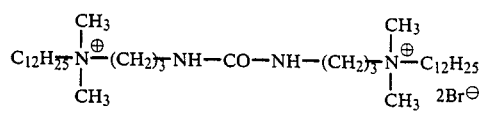

ANALYSIS: Found: Br⊖: 2.77 milliequivalents/gram; quaternary ammonium: 2.82 milliequivalents/gram. Theory: 2.75 milliequivalents/gram.

The following compounds are obtained under the operating conditions summarised in the table below:

EXAMPLE 2

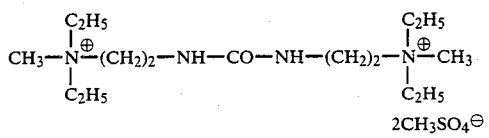

| Elementary analysis | C % | H % | N % | S % |
|---|---|---|---|---|
| Calculated (1H₂O) | 38.64 | 8.33 | 10.6 | 12.12 |
| Found | 39.15 | 8.40 | 10.13 | 12.41 |

EXAMPLE 3

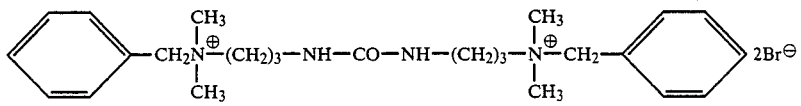

ANALYSIS: Found: Br⊖: 3.42 milliequivalents/gram; quaternary ammonium: 3.44 milliequivalents/gram. Theory: 3.50 milliequivalents/gram.

EXAMPLE 4

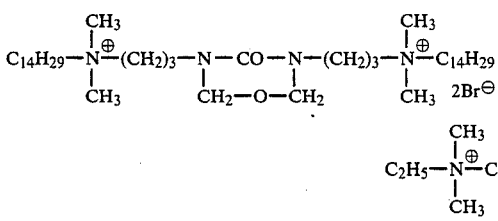

ANALYSIS: Melting point: softening above 150° C. Found: Br⊖: 2.51 milliequivalents/gram; quaternary ammonium: 2.62 milliequivalents/gram; Theory: 2.42 milliequivalents/gram.

EXAMPLE 5

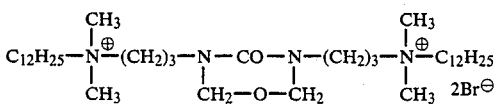

ANALYSIS: Melting point: 170° C. Found: Br⊖: 2.58 milliequivalents/gram; quaternary ammonium: 2.58 milliequivalents/gram. Theory: 2.60 milliequivalents/gram.

EXAMPLE 6

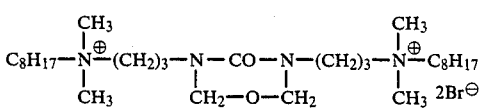

ANALYSIS: Melting point: 140° C. Found: Br⊖: 3.07 milliequivalents/gram; quaternary ammonium: 3.05 milliequivalents/gram. Theory: 3.04 milliequivalents/gram.

EXAMPLE 7

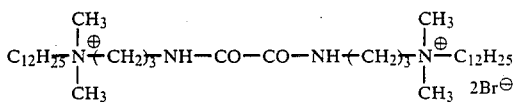

ANALYSIS: Melting point: 204° C. Found: Br⊖: 2.62 milliequivalents/gram; quaternary ammonium: 2.64 milliequivalents/gram. Theory: 2.65 milliequivalents/gram.

EXAMPLE 8

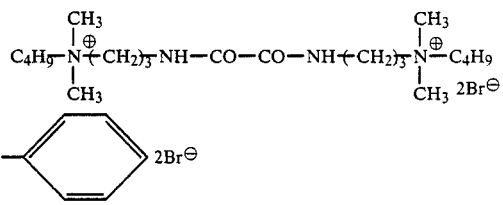

ANALYSIS: Melting point: 152° C. Found: Br⊖: 3.76 milliequivalents/gram; quaternary ammonium: 3.76 milliequivalents/gram. Theory: 3.76 milliequivalents/gram.

EXAMPLE 9

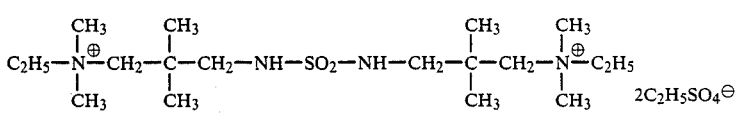

ANALYSIS: 1H NMR spectrum compatible with the proposed structure.

EXAMPLE 10

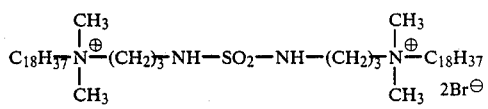

ANALYSIS: Melting point: 130° C. Found: Br⊖: 2 milliequivalents/gram; quaternary ammonium: 2.13 milliequivalents/gram. Theory: 2.14 milliequivalents/gram.

EXAMPLE 11

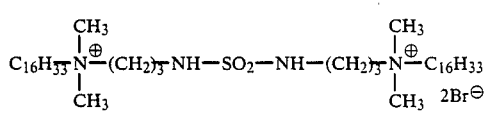

ANALYSIS: Melting point: 130° C. Found: Br⊖: 2.30 milliequivalents/gram; quaternary ammonium: 2.26 milliequivalents/gram. Theory: 2.28 milliequivalents/gram.

EXAMPLE 12

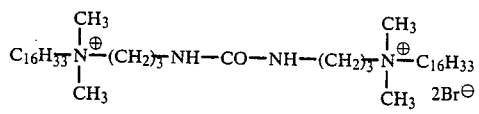

ANALYSIS: Melting point: 110° C. Found: $Br^{\ominus}$: 2.42 milliequivalents/gram; quaternary ammonium: 2.36 milliequivalents/gram. Theory: 2.38 milliequivalents/gram.

EXAMPLE 13

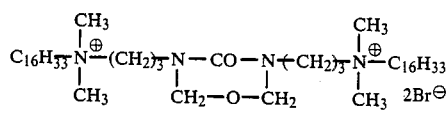

ANALYSIS: Melting point: 170° C. Found: $Br^{\ominus}$: 2.28 milliequivalents/gram; quaternary ammonium: 2.25 milliequivalents/gram. Theory: 2.27 milliequivalents/gram.

| | Conditions for the preparation of the compounds described in Examples Nos. 2 to 13 | | |
|---|---|---|---|
| | Ratio Quaternising agent | Amount of acetone used, | Reaction time |
| Example No. | Ditertiary diamine | in cm³ per mol of amine | under acetone reflux, in hours |
| 2 | 2 | 1,875 | 1 |
| 3 | 2.24 | 2,000 | 4 |
| 4 | 2.5 | 2,000 | 22 |
| 5 | 2.5 | 2,000 | 14 |
| 6 | 2 | 2,500 | 33 |
| 7 | 2 | 6,000 | 56 |
| 8 | 2 | 3,300 | 20 |
| 9 | 2.02 | 4,650 | 105 |
| 10 | 2 | 3,750 | 22 |
| 11 | 2.2 | 3,750 | 32 |
| 12 | 2.5 | 4,500 | 19 |
| 13 | 2.5 | 2,500 | 31 |

Composition Examples

EXAMPLE 14

Shampoo

The following composition is prepared:

| | |
|---|---|
| Compound of Example 1 | 0.5 g (of active ingredient) |
| Non-ionic surface-active agent based on polyglycerolated (4.2 mols) lauryl alcohol of the statistical formula: $C_{12}H_{25}\text{—}(OCH_2CH\text{—})_{4.2}\text{OH}$ $\quad\quad\quad\quad\quad\quad\quad\quad\mid$ $\quad\quad\quad\quad\quad\quad\quad\quad CH_2OH$ | 5.0 g (of active ingredient) |
| Non-ionic surface-active agent of the formula: $R\text{—}CHOH\text{—}CH_2O\text{—}(CH_2\text{—}CHOH\text{—}CH_2O)_{\overline{n}}H$ R = mixture of $C_9$-$C_{12}$ alkyl radicals n = 3.5, statistical value | 10.0 g (of active ingredient) |
| Lauryl diethanolamide | 2.0 g (of active ingredient) |
| Water q.s.p. | 100 g |

The pH is adjusted to 7.1 with HCl. About 10 cm³ of this shampoo are applied to a head of hair wetted beforehand. The hair is massaged lightly. It is rinsed with water, a second application is carried out and the hair is massaged vigorously to obtain a copious foam and, after an interval of a few minutes, is rinsed.

The hair is easy to comb out when wet. When dry, the hair is shiny, soft to the touch, light and bouncy and has hold and bulk.

EXAMPLE 15

Shampoo

The following composition is prepared:

| | |
|---|---|
| Compound of Example 4 | 0.3 g (of active ingredient) |
| Dehyton AB 30 | 10.0 g |
| Aromox C.12 | 3.0 g (of active ingredient) |
| Copra diethanolamide | 2.0 g (of active ingredient) |
| Water q.s.p. | 100 g |

The pH is adjusted to 7.4 with NaOH. After application to the hair as indicated in Example 14, similar results are obtained.

EXAMPLE 16

Shampoo

The following composition is prepared:

| | |
|---|---|
| Compound of Example 5 | 0.9 g (of active ingredient) |
| Non-ionic surface-active agent of the Formula: $R\text{—}CHOH\text{—}CH_2O\text{—}(CH_2CHOH\text{—}CH_2\text{—}O)_{\overline{n}}H$ R = mixture of $C_9$-$C_{12}$ alkyl radicals n = 3.5, statistical value | 12.0 g (of active ingredient) |
| Polysorbate 20 | 8.0 g (of active ingredient) |
| Water q.s.p. | 100 g |

The pH is adjusted to 6 with NaOH. After application to the hair as indicated in Example 14, analogous results are observed.

EXAMPLE 17

Shampoo

The following composition is prepared:

| | |
|---|---|
| Compound of Example 2 | 0.4 g (of active ingredient) |
| Sodium salt of sulphated alkanol ($C_{12}$-$C_{14}$) oxyethyleneated with 2.2 mols of E.O. (ethylene oxide) containing 25% of active ingredient | 25 g |
| Miranol C2M (solution containing 40% of active ingredient) | 5.0 g |
| Copra diethanolamide | 2.0 g (of active ingredient) |
| Water q.s.p. | 100 g |

The pH is adjusted to 8.1 with lactic acid. After application to wet hair as indicated in Example 14, the same results are obtained.

EXAMPLE 18

Shampoo

The following composition is prepared:

| | |
|---|---|
| Compound of Example 3 | 3 g (of active ingredient) |
| Non-ionic surface-active agent based on polyglycerolated (4.2 mols) lauryl alcohol of the statistical formula: | 10 g (of active ingredient) |

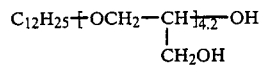

| | |
|---|---|
| Polyoxyethyleneated lauryl alcohol containing 12 mols of E.O. | 5 g (of active ingredient) |
| Lipoproteol LCO | 24 g |
| Water q.s.p. | 100 g |

The pH is adjusted to 7 with lactic acid. After application to wet hair as indicated in Example 14, similar results are obtained.

EXAMPLE 19

Shampoo

The following composition is prepared:

| | |
|---|---|
| Compound of Example 7 | 2 g (of active ingredient) |
| Maypon 4 CT | 32 g |
| Polysorbate 20 | 8 g (of active ingredient) |
| Water q.s.p. | 100 g |

The pH is adjusted to 7.6 with triethanolamine.
After application to wet hair as indicated in Example 14, similar results are observed.

EXAMPLE 20

Shampoo

The following composition is prepared:

| | |
|---|---|
| Compound of Example 9 | 2.5 g (of active ingredient) |
| Miranol C2 M (solution containing 40% of active ingredient) | 13.0 g |
| Sandopan CTC AC | 8.9 g |
| Water q.s.p. | 100 g |

The pH is adjusted to 7 with triethanolamine.
After application to wet hair as indicated in Example 14, similar results are observed.

EXAMPLE 21

Shampoo

The following composition is prepared:

| | |
|---|---|
| Compound of Example 6 | 1.5 g (of active ingredient) |
| Sodium lauryl-ether-sulphate containing 30% of active ingredient | 20.0 g |
| Sodium salt of sulphated alkanol($C_{12}$-$C_{14}$) oxyethyleneated with 2.2 mols of E.O., containing 25% of active ingredient | 10.0 g |
| NaCl | 1.5 g |
| Water q.s.p. | 100 g |

The pH is adjusted to 8.1 with NaOH. After application to wet hair as indicated in Example 14, analogous results are observed.

EXAMPLE 22

Rinsing Lotion

The following composition is prepared:

| | |
|---|---|
| Compound of Example 5 | 2.5 g |
| Cetyl alcohol | 5.0 g |
| Cetyl/stearyl alcohol containing 15 mols of E.O. | 3.0 g |
| Cellosize QP 4400 H | 0.4 g |
| Ammonyx 27 | 2.0 g |
| Water q.s.p. | 100 g |

The pH is adjusted to 6.2 with NaOH.
After the hair has been shampooed, rinsed and towel-dried, the above lotion is applied to the clean hair.
This lotion is suitably spread over the whole head of hair and, after an interval of about 10 minutes, the hair is rinsed very carefully. When wet, the hair is easy to comb out and is soft to the touch. When dry, the hair is soft, shiny, light and not charged with static electricity. It has hold and bulk.

EXAMPLE 23

Rinsing Lotion

The following composition is prepared:

| | |
|---|---|
| Compound of Example 4 | 1 g |
| Mixture of cetyl and stearyl alcohols (50/50) | 2 g |
| Cetyl/stearyl alcohol containing 15 mols of E.O. | 3 g |
| Cellosize QP 4400 H | 0.8 g |
| Ammonyx 4002 | 1.5 g |
| Water q.s.p. | 100 g |

The pH is adjusted to 5.3 with triethanolamine. After application to clean wet hair as indicated in Example 22, similar results are observed.

EXAMPLE 24

Gel For Oxidation Dyeing

The following composition is prepared:

| | |
|---|---|
| Triethanolamine lauryl-sulphate containing 40% of active ingredient | 2.5 g |
| Eutanol G | 7.5 g |
| Oleyl diethanolamide | 7.0 g |
| Mergital OC 30 | 3.0 g |
| Compound of Example 8 | 2.5 g |
| Oleic acid | 20.0 g |
| Benzyl alcohol | 10.0 g |
| 96° strength ethyl alcohol | 10.0 g |
| 22° Bé strength ammonia solution | 18 ml |
| N,N—Bis-(2-hydroxyethyl)-para-phenylene-diamine sulphate | 1 g |
| p-Aminophenol | 0.4 g |
| Resorcinol | 0.15 g |
| m-Aminophenol | 0.10 g |
| Alpha-naphthol | 0.40 g |
| Hydroquinone | 0.10 g |
| Ethylenediaminetetraacetic acid | 0.24 g |
| Sodium bisulphite solution (d = 1.32) | 1 ml |
| Water q.s.p. | 100 g |

30 g of this carrier are mixed in a bowl with 30 g of hydrogen peroxide (20 volumes). This gives a consistent gel which is pleasant to apply and which adheres well to the hair.

It is applied with the aid of a paintbrush.

After an interval of 30 to 40 minutes, the hair is rinsed.

The hair is easy to comb out. It has a silky feel. It is set in waves and dried. The hair is shiny, bouncy and has body (volume); it has a silky feel and is easy to comb out.

An ashen deep blond shade is obtained.

EXAMPLE 25

Gel For Oxidation Dyeing

The following composition is prepared:

| | |
|---|---|
| Non-ionic surface-active agent of the formula: | |
| R—O—$(C_2H_3O(CH_2OH))_2$H | 20 g |
| R = oleyl radical | |
| Non-ionic surface-active agent of the formula: | |
| R—O—$(C_2H_3O(CH_2OH))_4$H | 20 g |
| R = oleyl radical | |
| Oleyl diethanolamide | 12 g |
| Compound of Example 3 | 3 g |
| 96° strength ethyl alcohol | 12 g |
| Butylglycol | 1 g |
| Propylene glycol | 2 g |
| Pentasodium salt of diethylenetriamine-pentaacetic acid (40% of active ingredient) | 2.5 g |
| 22° Bé strength ammonia solution | 9 ml |
| 1-Amino-4-(2-methoxyethyl)-aminobenzene dihydrochloride | 1.6 g |
| p-Aminophenol | 0.3 g |
| Resorcinol | 0.2 g |
| m-Aminophenol | 0.25 g |
| 5-N—(2-Hydroxyethyl)-amino-2-methylphenol | 0.02 g |
| 1-(2-Hydroxyethoxy)-2,4-diaminobenzene dihydrochloride | 0.02 g |
| Sodium bisulphite solution (d = 1.32) | 1 ml |
| Water q.s.p. | 100 g |

30 g of this carrier are mixed in a bowl with 30 g of hydrogen peroxide (20 volumes).

This gives a gel which is pleasant to apply and which adheres well to the hair.

It is applied with the aid of a paintbrush.

After an interval of 30 to 40 minutes, the hair is rinsed.

The hair is easy to comb out. It has a silky feel. An ashen light chestnut shade is obtained.

EXAMPLE 26

Hair-Care Cream

The following composition is prepared:

| | |
|---|---|
| Cetyl alcohol | 17 g |
| Sodium cetyl-/stearyl-sulphate | 6 g |
| Cetyl/stearyl alcohol containing 15 mols of E.O. | 4 g |
| Oleyl alcohol | 4 g |
| Compound of Example 4 | 2 g |
| Water q.s.p. | 100 g |

30 to 50 g of this cream are applied to clean damp hair which has been towel-dried, care being taken to impregnate the head of hair well.

After an interval of 15 minutes, the hair is rinsed.

When wet, the hair is easy to comb out and has a soft feel.

It is set in waves and dried under a hood. When dry, the hair is easy to comb out and has a silky feel. It is shiny and bouncy.

EXAMPLE 27

Lightening Gel

The following composition is prepared:

| | |
|---|---|
| Eutanol G | 8 g |
| Triethanolamine lauryl-sulphate containing 40% of active ingredient | 3 g |
| Oleyl diethanolamide | 6 g |
| Hydrogenated tallow amide containing 50 mols of E.O. | 3.5 g |
| Oleic acid | 18 g |
| Compound of Example 2 | 3 g |
| 96° strength ethyl alcohol | 15 g |
| Propylene glycol | 12 g |
| 22° Bé strength ammonia solution | 16 ml |
| Ethylenediaminetetraacetic acid sold under the name TRILON B | 0.3 g |
| Water q.s.p. | 100 g |

Before use, 40 g of this formulation are mixed in a bowl with 40 g of hydrogen peroxide (30 volumes).

This gives a gel which is pleasant to apply and which adheres well to the hair. After an interval of 30 to 45 minutes, the hair is rinsed.

When wet, the hair is easy to comb out and has a silky feel. After drying, it is shiny, has a silky feel and is easy to comb out.

On deep chestnut hair, a deep blond is obtained after bleaching.

EXAMPLE 28

Restructuring Lotion

Before use, 0.3 g of dimethylolethylenethiourea is mixed with 20 ml of a solution containing:

| | |
|---|---|
| Compound of Example 9 | 1.5 g |
| Water q.s.p. | 100 g |
| HCl q.s.p. | pH 2.7 |

The mixture is applied to washed hair which has been towel-dried, and then the hair is set in waves.

The hair is easy to comb out and has a soft feel.

It is set in waves and dried.

The hair is shiny and easy to comb out and has a silky feel.

EXAMPLE 29

Wavesetting Lotion

| | |
|---|---|
| Polyvinylpyrrolidone VA S 630 from GAF | 1.5 g |
| Compound of Example 4 | 1 g |
| Ethyl alcohol q.s.p. | 15° |
| Water q.s.p. | 100 ml |

This composition is applied to clean wet hair. The hair is set in waves and dried. The hair is shiny and has hold and bulk. It is soft to the touch and easy to comb out.

EXAMPLE 30

Perming Composition

| REDUCING LIQUID | |
|---|---|
| Thioglycolic acid | 8 g |
| Ammonia q.s.p. | neutralisation |
| Ammonium bicarbonate | 7 g |
| Pentasodium salt of diethylenetriamine-pentaacetic acid | 0.2 g |
| Polyoxyethyleneated oleyl ether containing 20 mols of ethylene oxide | 1 g |
| Compound of Example 1 | 2 g |
| Perfume | 0.3 g |
| Deionised water q.s.p. | 100 ml |
| NEUTRALISER | |
| Hydrogen peroxide q.s.p. | 8 volumes strength |
| Stabilizers | 0.2 g |
| Polyoxyethyleneated nonylphenol containing 9 mols of ethylene oxide | 1 g |
| Perfume | 0.3 g |
| Citric acid q.s.p. | pH 3 |
| Deionised water q.s.p. | 100 ml |

The reducing liquid is applied to wet hair which has been wound onto rollers. It is left to act for 5 to 30 minutes, the hair is rinsed and the neutraliser is applied. The latter is left to act for 5 to 30 minutes and the hair is rinsed again. The hair treated in this way is soft to the touch and easy to comb out.

EXAMPLE 31

Perming Composition

| REDUCING LIQUID | |
|---|---|
| Thioglycolic acid | 5 g |
| Ammonium bicarbonate | 8.5 g |
| Pentasodium salt of diethylene-triaminepentaacetic acid | 0.2 g |
| Protein hydrolysate | 1 g |
| Polyoxyethyleneated oleyl ether containing 20 mols of ethylene oxide | 1 g |
| Perfume | 0.3 g |
| Deionised water q.s.p. | 100 ml |
| NEUTRALISER | |
| Hydrogen peroxide q.s.p. | 8 volumes strength |
| Stabilizers | 0.2 g |
| Polyoxyethyleneated nonylphenol containing 9 mols of ethylene oxide | 1 g |
| Compound of Example 1 | 1 g |
| Citric acid q.s.p. | pH 3 |
| Perfume | 0.3 g |
| Deionised water q.s.p. | 100 ml |

By following the same procedure as in Example 30, analogous results are observed after the perming treatment.

The tradenames used in the examples are explained below.

DEHYTON AB 30: 30% strength $C_{12}$–$C_{18}$-alkyl-dimethylcarboxymethylammonium hydroxide sold by HENKEL.

AROMOX C12: Solution of copra bis-(2-hydroxyethyl)-amine oxide in a water/isopropanol mixture (50/50), sold by AKZO.

POLYSORBATE 20: Polyoxyethykleneated (20) sorbitan monolaurate sold by ATLAS.

MIRANOL C2M: Cycloimidazoline derivative containing 40% of active ingredient, of the formula:

$$C_{11}H_{23}-\underset{\underset{CH_2}{\overset{N}{\|}}}{C}-\underset{\underset{}{CH_2}}{N^\oplus}\underset{}{\overset{CH_2-COONa}{\diagup}}\underset{}{\diagdown}{CH_2-CH_2OCH_2-COO^\ominus},$$

sold by MIRANOL.

LIPOPROTEOL LCO: Mixed sodium and triethanolamine salts of lipoaminoacids obtained by combining lauric acid with aminoacids derived from the total hydrolysis of collagen. Product containing 22% of active ingredient, sold by RHONE POULENC.

MAYPON 4 CT: Triethanolamine salt of the condensation product of copra acid and animal protein hydrolysate. Product containing 40% of active ingredient, sold by STEPAN.

SANDOPAN CTC AC: Trideceth-7 carboxylic acid of the formula:

$$CH_3-(CH_2)_{11}-CH_2-(OCH_2-CH_2)_6-OCH_2-COOH,$$

containing 90% of active ingredient, sold by SANDOZ.

CELLOSIZE QP 4400H: Hydroxyethylcellulose sold by UNION CARBIDE.

AMMONYX 27: Monoalkyltrimethylammonium chloride (alkyl=tallow radical) sold by FRANCONYX.

AMMONYX 4002: Stearyldimethylbenzylammonium chloride sold by FRANCONYX.

EUTANOL G: 2-Octyldodecanol marketed by HENKEL.

MERGITAL OC 30: Oleyl/cetyl alcohol containing 30 mols of E.O., marketed by HENKEL.

We claim:

1. A composition suitable for treating hair, skin and nails which comprises at least one bis-(quaternary ammonium) derivative having the formula:

$$R_3-\underset{\underset{R_2}{|}}{\overset{\overset{R_1}{|}}{N^\oplus}}-A_1-\underset{\underset{R_6}{|}}{N}-Z-\underset{\underset{R_7}{|}}{N}-A_2-\underset{\underset{R_5}{|}}{\overset{\overset{R_4}{|}}{N^\oplus}}-R_3 \quad 2X^\ominus \qquad (I)$$

in which $R_1$, $R_2$, $R_4$ and $R_5$ are identical or different and denote lower alkyl or lower hydroxyalkyl radicals, $R_3$ denotes an alkyl, cycloalkyl, alkenyl, hydroxyalkyl or aralkyl radical containing a maximum of 20 carbon atoms, $A_1$ and $A_2$, which are identical or different, denote alkylene or arylene radicals containing a maximum of 20 carbon atoms, Z denotes $-SO_2-$, $R_6$ and $R_7$, which are identical for different, represent hydrogen atoms or lower alkyl radicals, and $X^\ominus$ denotes an inorganic or organic anion of a low molecular weight acid, and at least one cosmetic adjuvant selected from non-ionic, anionic, cationic or amphoteric surface-active agents, animal, mineral, vegetable or synthetic oils or waxes, fatty alcohols, anionic, cationic, non-ionic or amphoteric resins, emulsifiers, organic solvents, thickeners, opacifiers, preservatives, perfumes, agents for imparting pearlescence, sequestering agents, antioxidants, pH modifiers, electrolytes, and hair restructuring agents, said bis-(quaternary ammonium) derivative being present in an amount of 0.01 to 10% by weight of said composition.

2. A composition according to claim 1, in which $R_1$, $R_2$, $R_4$ and $R_5$ denote a methyl or ethyl radical.

3. A composition according to claim 1 in which $R_3$ denotes a $C_8$ to $C_{18}$ alkyl radical.

4. A composition according to claim 1 in which $A_1$ and $A_2$ denote an ethylene or trimethylene radical.

5. A composition according to claim 1 for use in the treatment of the hair which is in a form selected from the group consisting of an aqueous, alcoholic or aqueous-alcoholic solution, a cream, a gel, an emulsion, a powder and a product packaged in an aerosol.

6. A composition according to claim 5 which is in the form of an aqueous solution.

7. A composition according to claim 1 which contains 0.1 to 5% by weight of compound of formula (I).

8. A shampoo composition which facilitates the combing out of the hair when wet or dry and which imparts hold, softness, shine, suppleness, manageability and antistatic properties to the hair when dry, said composition comprising, in an aqueous medium, at least one bis-(quaternary ammonium) derivative having the formula:

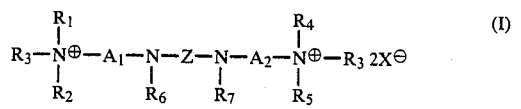

in which $R_1$, $R_2$, $R_4$ and $R_5$ are identical or different and denote lower alkyl or lower hydroxyalkyl radicals, $R_3$ denotes an alkyl, cycloalkyl, alkenyl, hydroxyalkyl or aralkyl radical containing a maximum of 20 carbon atoms, $A_1$ and $A_2$, which are identical or different, denote alkylene or arylene radicals containing a maximum of 20 carbon atoms, Z denotes $-SO_2-$, $R_6$ and $R_7$, which are identical or different, represent hydrogen atoms or lower alkyl radicals, and $X^\ominus$ denotes an inorganic or organic anion of a low molecular weight acid, said bis-(quaternary ammonium) derivative being present in an amount of 0.01 to 10% by weight of said composition; and at least one anionic, non-ionic or amphoteric surface active agent or a mixture thereof, said surface-active agent being present in an amount ranging from 2 to 50% by weight of said shampoo composition.

9. A composition according to claim 8, in which $R_1$, $R_2$, $R_4$ and $R_5$ denote a methyl or ethyl radical.

10. A composition according to claim 8 in which $R_3$ denotes a $C_8$ to $C_{18}$ alkyl radical.

11. A composition according to claim 8 in which $A_1$ and $A_2$ denote an ethylene or trimethylene radical.

12. A composition according to claim 8 which also contains a cationic surface-active agent.

13. A rinsing composition which facilitates the combing out of the hair when wet or dry and imparts hold, softness, shine, suppleness, manageability and antistatic properties to the hair when dry, which comprises, in an aqueous, alcoholic, or aqueous-alcoholic medium, at least one bis-(quaternary ammonium) derivative having the formula:

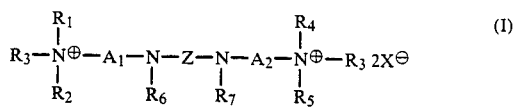

in which $R_1$, $R_2$, $R_4$ and $R_5$ are identical or different and denote lower alkyl or lower hydroxyalkyl radicals, $R_3$ denotes an alkyl, cycloalkyl, alkenyl, hydroxyalkyl or aralkyl radical containing a maximum of 20 carbon atoms, $A_1$ and $A_2$, which are identical or different, denote alkylene or arylene radicals containing a maximum of 20 carbon atoms, Z denotes $-SO_2-$, $R_6$ and $R_7$, which are identical or different, represent hydrogen atoms or lower alkyl radicals, and $X^\ominus$ denotes an inorganic or organic anion of a low molecular weight acid, said bis-(quaternary ammonium) derivative being present in an amount of 0.01 to 10% by weight of said composition and said composition being in the form of a lotion, cream or gel having a pH ranging from 2 to 11.

14. A composition according to claim 13 which further contains an animal, mineral, vegetable or synthetic oil or wax.

15. A composition according to claim 13 which further contains an anionic, cationic, non-ionic or amphoteric resin.

16. A composition according to claim 13 which further contains a fatty alcohol.

17. A composition according to claim 13 which further contains a polyethyleneglycol or derivative thereof.

18. A composition according to claim 13 which further contains an effective amount of a hair restructuring agent.

19. Process for treating hair, skin or nails, which comprises applying thereto a composition as defined in claim 1.

20. A process according to claim 19 which further comprises allowing said composition to remain on said hair, skin or nails for 1 to 30 minutes and rinsing said hair, skin or nails.

* * * * *

UNITED STATES PATENT AND TRADEMARK OFFICE
CERTIFICATE OF CORRECTION

PATENT NO. : 4,828,819

DATED : May 9, 1989

INVENTOR(S) : Gerard LANG et al

It is certified that error appears in the above-identified patent and that said Letters Patent is hereby corrected as shown below:

On the title page:

In the heading and at Section [75], the inventor's surname "Lan" should correctly read -- Lang --.

Signed and Sealed this

Tenth Day of April, 1990

Attest:

HARRY F. MANBECK, JR.

*Attesting Officer*     *Commissioner of Patents and Trademarks*